United States Patent [19]

Terwilliger

[11] Patent Number: 5,752,923
[45] Date of Patent: May 19, 1998

[54] BIOPSY INSTRUMENT WITH HANDLE AND NEEDLE SET

[75] Inventor: Richard A. Terwilliger, Estes Park, Colo.

[73] Assignee: Medical Device Technologies, Inc., Gainesville, Fla.

[21] Appl. No.: 669,039

[22] Filed: Jun. 24, 1996

[51] Int. Cl.$^6$ .................. A61M 5/20; A61M 5/178; A61M 5/00

[52] U.S. Cl. .................. 600/562; 600/564; 600/565; 600/566; 600/567; 604/158; 604/159; 604/164; 604/171; 604/157

[58] Field of Search ............... 128/749, 751, 128/753, 754; 604/156, 158, 159, 164, 171, 157; 600/562, 564–67

[56] References Cited

U.S. PATENT DOCUMENTS

| Re. 34,056 | 9/1992 | Lindgren et al. . |
|---|---|---|
| 3,090,384 | 5/1963 | Baldwin et al. . |
| 3,732,858 | 5/1973 | Banko . |
| 3,788,320 | 1/1974 | Dye . |
| 3,844,272 | 10/1974 | Banko . |
| 4,210,146 | 7/1980 | Banko . |
| 4,266,555 | 5/1981 | Jamshidi . |
| 4,403,617 | 9/1983 | Tretinyak . |
| 4,476,864 | 10/1984 | Tezel . |
| 4,570,632 | 2/1986 | Woods . |
| 4,600,014 | 7/1986 | Beraha . |
| 4,640,296 | 2/1987 | Schnepp-Pesch et al. . |
| 4,651,752 | 3/1987 | Fuerst . |
| 4,655,226 | 4/1987 | Lee . |
| 4,699,154 | 10/1987 | Lindgren . |
| 4,733,671 | 3/1988 | Mehl . |
| 4,747,414 | 5/1988 | Brossel . |
| 4,776,346 | 10/1988 | Beraha et al. . |
| 4,817,631 | 4/1989 | Schnepp-Pesch et al. . |
| 4,924,878 | 5/1990 | Nottke . |
| 4,958,625 | 9/1990 | Bates et al. . |
| 5,025,797 | 6/1991 | Baran . |
| 5,064,411 | 11/1991 | Gordon, III . |
| 5,220,926 | 6/1993 | Jones . |

FOREIGN PATENT DOCUMENTS

| 0141108 | 4/1980 | German Dem. Rep. . |
|---|---|---|
| 159394 A | 9/1983 | German Dem. Rep. . |
| 0221 007 A1 | 5/1987 | German Dem. Rep. . |
| 287 650 A5 | 3/1991 | German Dem. Rep. . |
| 0010321 | 4/1980 | Germany . |
| 94 14 727.2 | 1/1995 | Germany . |
| 94 14 728.0 | 1/1995 | Germany . |
| 175611 | 6/1965 | U.S.S.R. . |
| 1551362 A1 | 3/1990 | U.S.S.R. . |
| 709714 | 6/1954 | United Kingdom . |
| 748451 | 5/1956 | United Kingdom . |
| WO 83/03343 | 10/1983 | WIPO . |

Primary Examiner—Vincent Millin
Assistant Examiner—Dinh X. Nguyen
Attorney, Agent, or Firm—Fliesler, Dubb, Meyer & Lovejoy

[57] ABSTRACT

A biopsy instrument 40 includes a handle 1 and a disposable biopsy needle set or needle cartridge 20. The needle set includes a cannula 9 with a cannula hub 8 and a stylet 7 with a stylet hub 6. The needle set 20 is positionable within the handle 1 and actuatable thereby for purposes of taking a biopsy tissue sample. The needle set 20 and in particular the hubs 6, 8, in combination with the handle 1, perform the actuation sequence which allows the needle to be projected into the tissue to be biopsied and the cannula to be subsequently urged over the needle to collect the tissue.

31 Claims, 16 Drawing Sheets

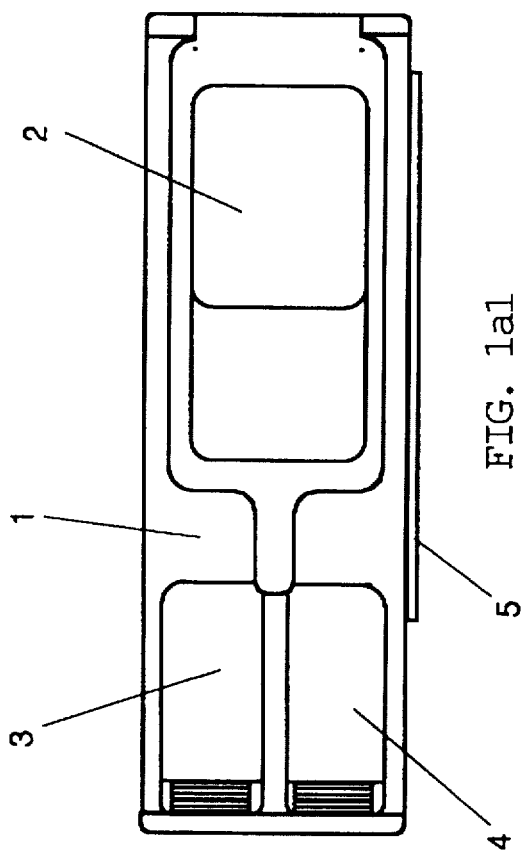
FIG. 1a1
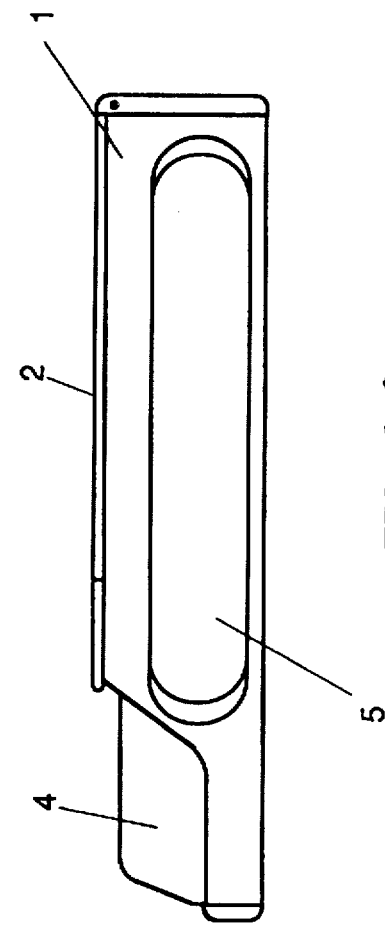
FIG. 1a2
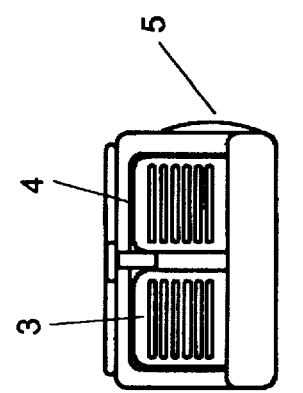
FIG. 1a3

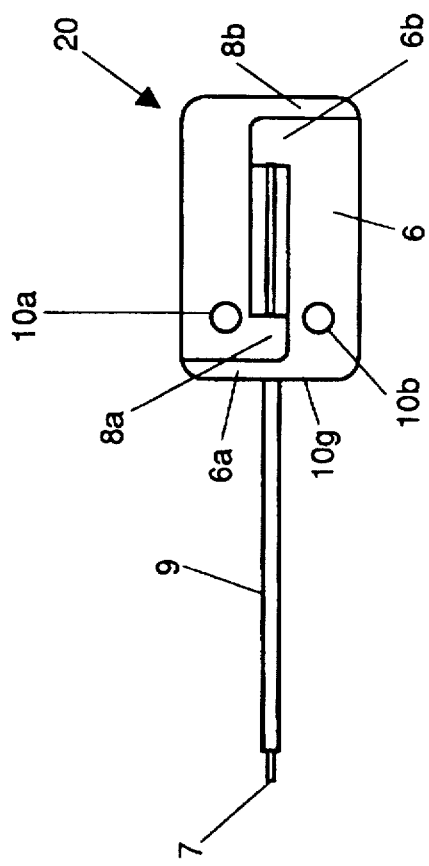
FIG 1b1
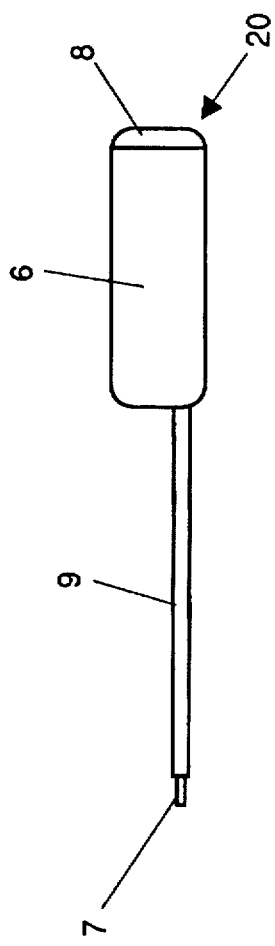
FIG 1b2
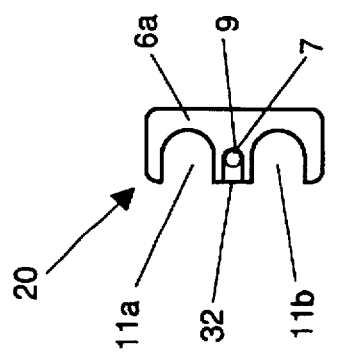
FIG 1b3

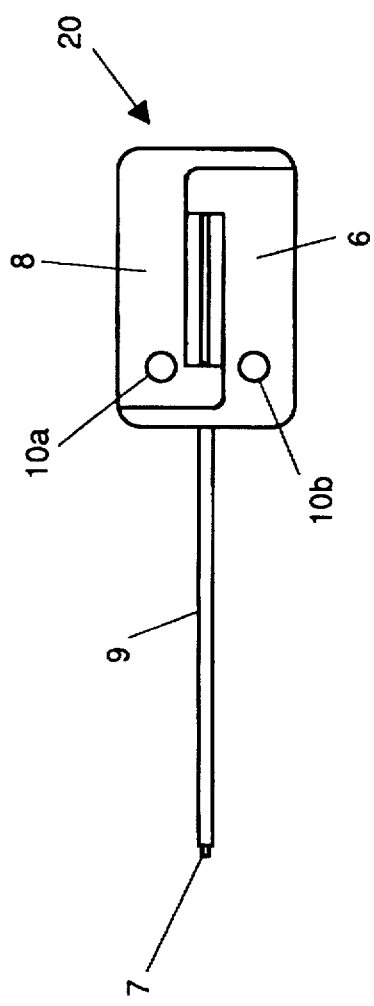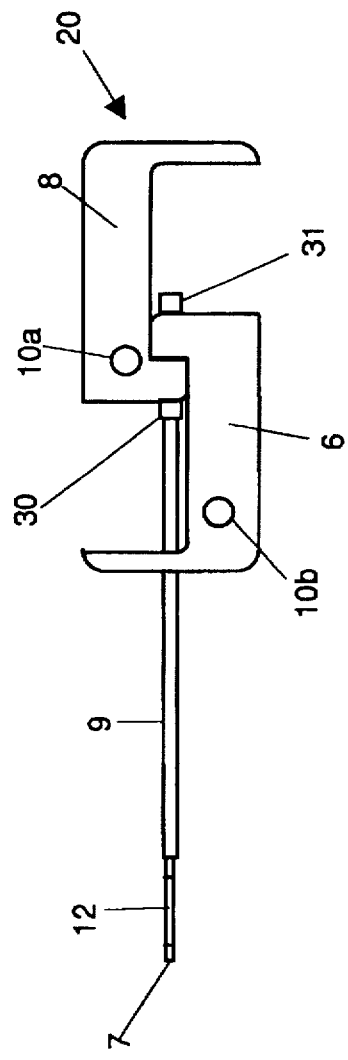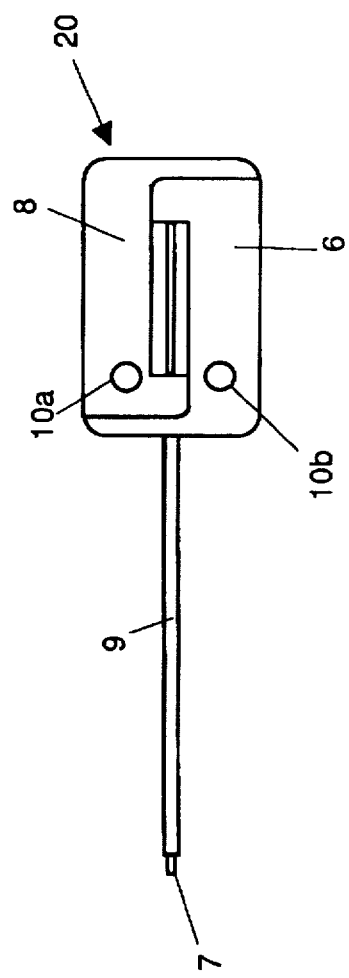

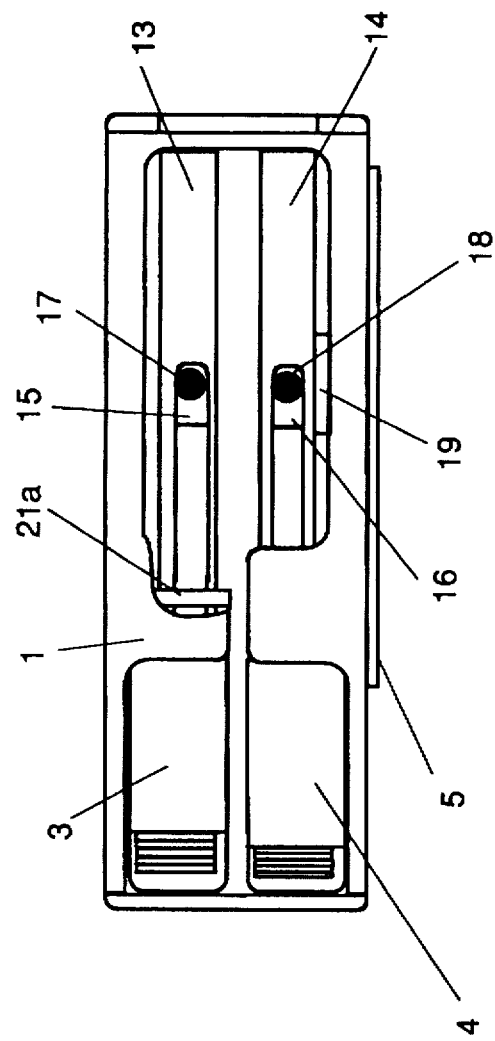
FIG 1d1
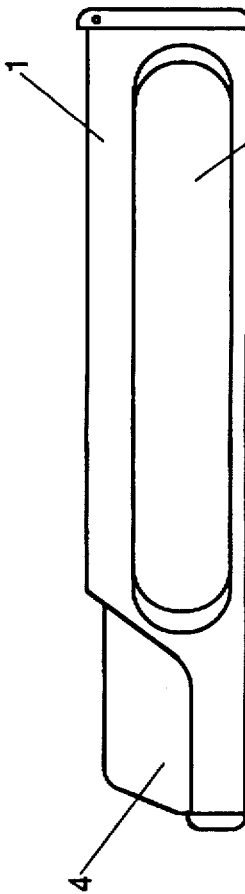
FIG 1d2
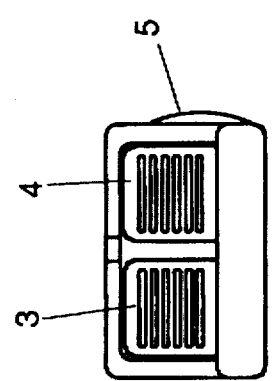
FIG 1d3

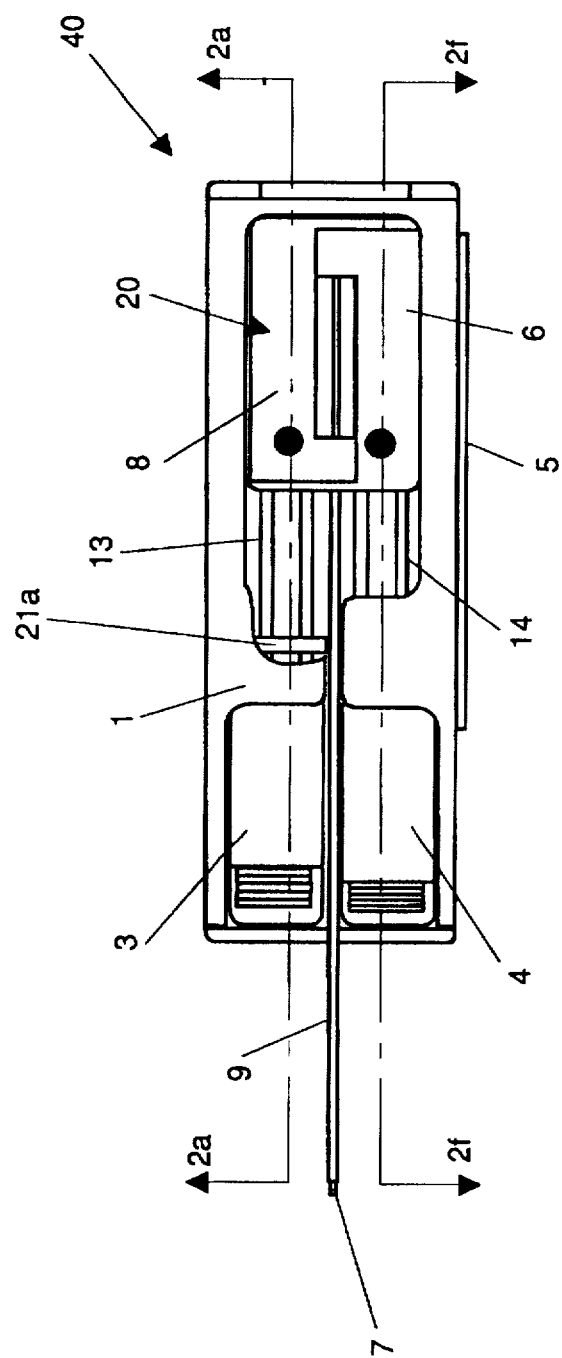
FIG 1f1
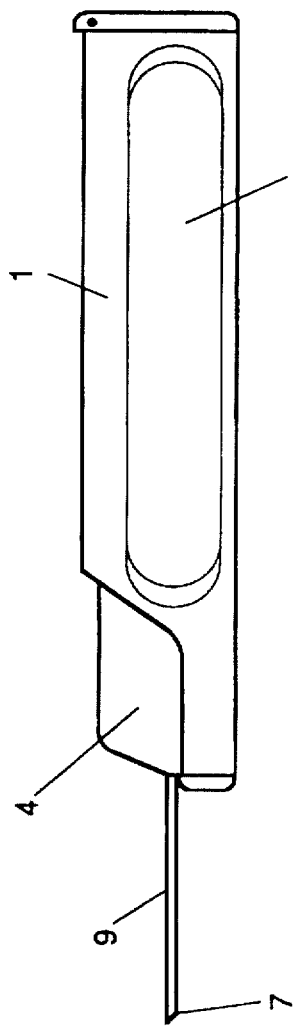
FIG 1f2
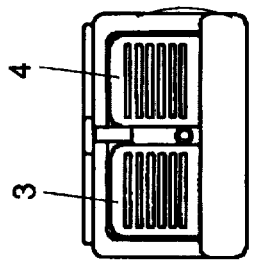
FIG 1f3

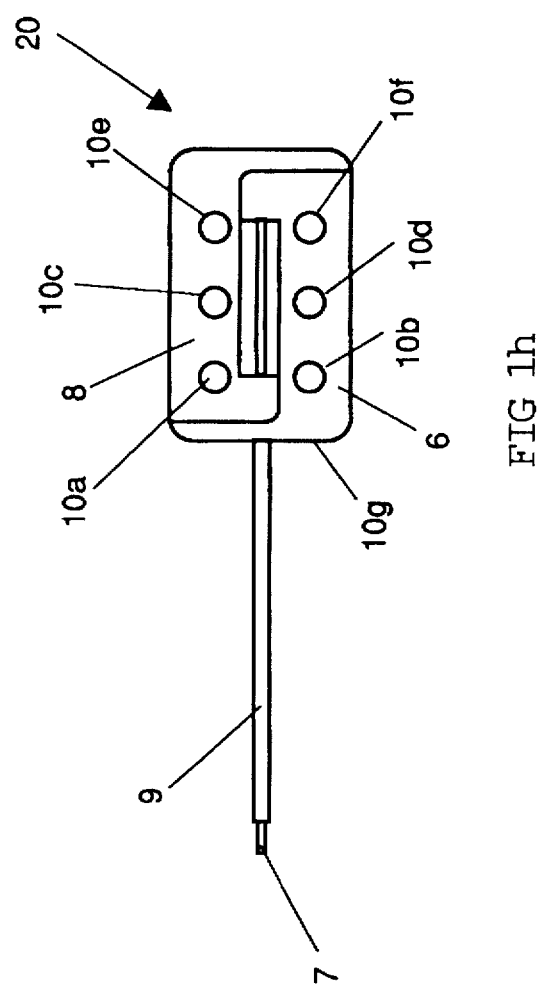

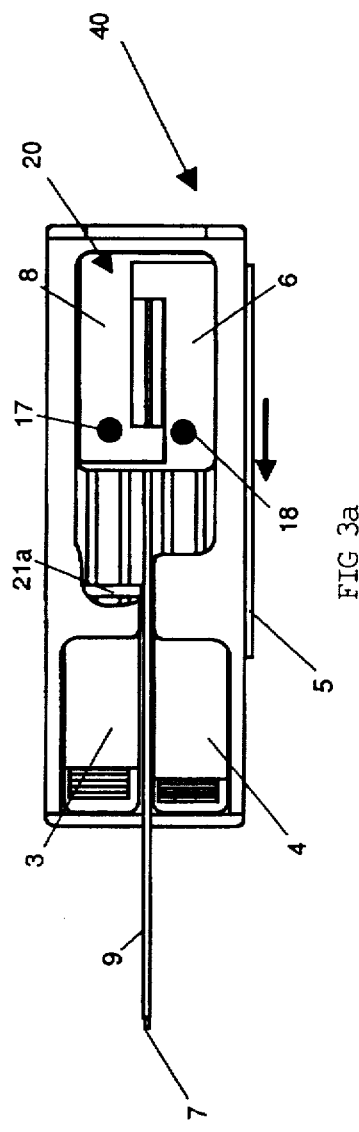
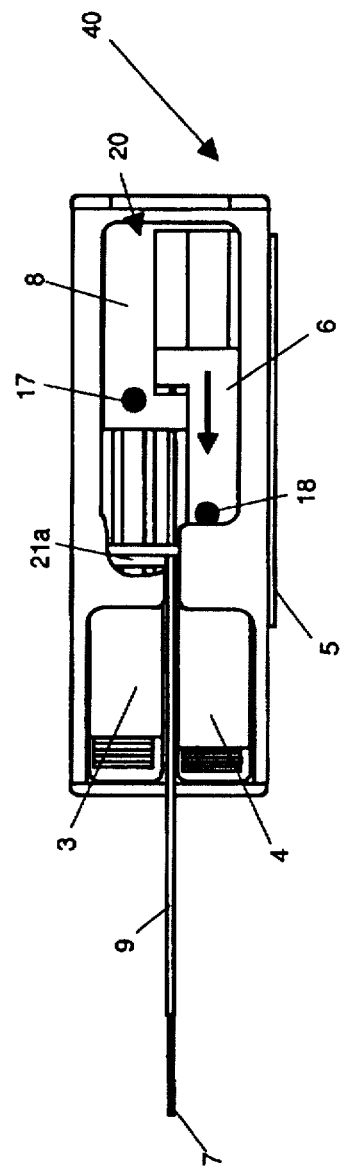
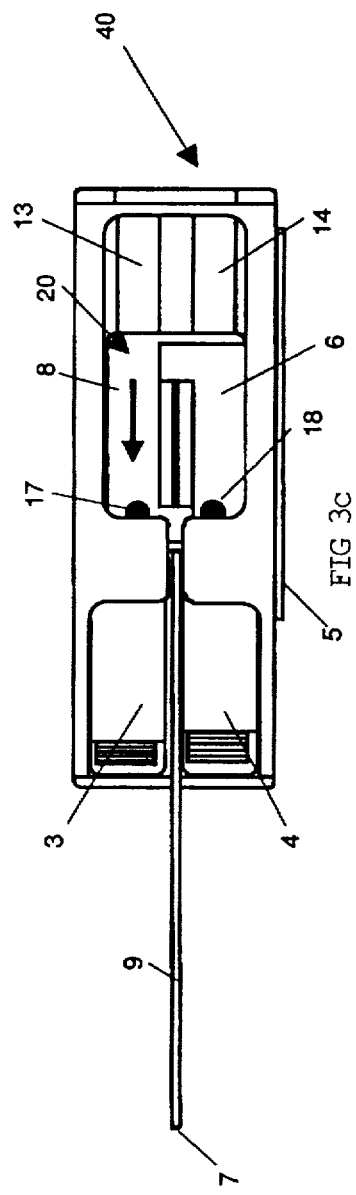

BIOPSY INSTRUMENT WITH HANDLE AND NEEDLE SET

FIELD OF THE INVENTION

This invention relates to an automated mechanism to collect a tissue sample from humans or animals by a procedure referred to as tissue biopsy, and more particularly to an instrument with an improved needle set which allows a more reliable way to obtain tissue cores automatically while performing tissue extraction from a tissue mass in a precise and rapid manner with minimum patient discomfort.

BACKGROUND OF THE INVENTION

It is often desirable and frequently absolutely necessary to sample or test a portion of tissue from humans and even animals to aid in the diagnosis and treatment of patients with cancerous tumors, premalignant conditions and other diseases or disorders. Typically in the case of cancer or the suspicion of malignant tumors, a very important process call tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways, palpation, x-ray imaging or ultrasound imaging. Once a tumor is identified, a biopsy procedure is performed. Modern medical opinion dictates early detection of cancer increases the likelihood of successful treatment. Biopsy are performed on "Tumor Masses" as small as 2 millimeters in diameter. This procedure is performed under ultrasound or x-ray guidance. Tumors of this size cannot be biopsied reliably by hand since the tumor is about the same size as the biopsy needle. Manual attempts at biopsy can push the tumor away without piercing the mass. Automatic puncture devices are needed to accelerate the needle at such a velocity that even a small tumor can be pierced.

Two very important innovations in the field of medical technology have influenced the field of tissue biopsy in the last five years.

One, the use of tissue imaging device which allow the physician to "see" inside the body and visually guide the needle to the tumor mass.

Two, the invention of the Automatic Core Biopsy Device (ACBD) or "Biopsy Gun". The ACBD is an instrument which propels a needle set with considerable force and speed to pierce the tumor mass and collect the tissue sample. This ACBD device has allowed physicians to test tissue masses in the early stages of growth and has contributed to the medical trend of early diagnosis and successful treatment of cancer.

Examples of such ACBD devices have been described and used for obtaining tissue samples in U.S. Pat. Nos. 4,651,752, 4,702,260, and 4,243,048.

Historically, Automated Core Biopsy Devices (ACBD) have used the "Tru-Cut" needle set design. The "Tru-Cut" needle is comprised of an inner notched stylet with an outer cannula. The stylet is advanced into the tissue under spring power followed by the cannula which cuts and traps the tissue sample in the notch of the stylet. The "TruCut" needle yields a core sample which is semi-circular in cross section with length of the core sample determined by the stroke of the ACBD.

The stylet is a needle with a notched cut out at the distal end. The cannula is a hollow needle with an angled cutting surface at the distal end which slides over the stylet. When the stylet is pushed into tissue, the tissue is pierced and relaxes into the notched cut out. When the cannula is slid forward, the tissue in the notch of the stylet is sliced off and retained in the notch until the cannula is drawn back.

Subsequent improvements to the "Tru-Cut" needle design have been introduced and are described in U.S. Pat. No. 5,449,001.

ACBD devices have been designed as totally disposable devices for single patient use and as reusable handles that accommodate a disposable needle set. In the era of managed health care, the cost of biopsy procedures has come under scrutiny. The disposable single use devices are expensive due to their high single use cost and also the reusable handles have, in prior art, been costly to obtain because of the expense of manufacturing a complicated mechanical design.

The prior art designs of the ACBD have relied on holders or carriers of specific design within the mechanism in order to secure the needle set. These carriers are guided by bushings that run on high tolerance guide rods within the mechanism. A sequence of specific motions are required to activate the needle set in such a manner so as to capture tissue within the notched stylet. The many mechanical parts required to guide and sequence the needles have led to complex designs that are large, costly and have low reliability.

The mechanism of the prior art ACBD is designed to have a stylet carrier that moves forward first and then activate the cannula carrier, thus advancing the needles in their proper sequence. These prior art devices require many high tolerance mechanical moving parts with precision bushings in order to have the device operate properly. The required repeated use of the reusable design requires that the mechanical design be robust and operate many cycles without undue wear or failure. These requirements have produced in prior designs, ACBDs that are heavy, large and costly due to their complicated mechanical designs.

To actuate the mechanism each prior art design has a unique actuator button or trigger. Some prior art devices have positioned this trigger at the rear of the housing and some on the side of the housing. One prior art device has two triggers, one at the back and one at the front of the housing. Each location has its advantages and disadvantages in helping the physician actuate the mechanism in the best way. Different biopsy procedure require different hand positions in which to hold the device for easiest operation.

In prior art designs, if the physician required a biopsy device which would cycle the needle set a short or longer distance into the tissue mass, either (1) a separate device for each needle distance desired had to be purchased, or (2) a prior art device that was capable of functioning at different distance settings had to be used. Such an adjustable device is mechanically complicated and requires external settings to be made to allow the mechanism to perform at different needle advancement distances.

The reusable handle ACBDs are used in many applications. Their use with imaging systems to guide the needle set to the point of biopsy is a valuable technique.

In Computer Aided Tomography (CAT scanning), the detachable needle set, that is used with reusable handle ACBDs, is placed manually into the patient and its location is verified with a CAT scan. The patient is then removed from the CAT scanner, the needle set is attached to the handle, and the mechanism of the ACBD is activated to perform the biopsy.

In order to maintain orientation of the needles as they relate to the mechanism of the ACBD, in some devices a separate "needle spacer" is attached to the needle set. This spacer maintains the relative position of the needles to each other as they are introduced into the body. Once the needle set is in place, the spacer must be removed from the needle set so the ACBD mechanism can cycle the needles and obtain a tissue sample.

The size, weight and expense of reusable prior art ACBD's have limited their use. An improved design is needed that gives the physician a small, light weight, easy to operate and cost effective design that improves the function and reduces the overall cost of the biopsy procedure.

SUMMARY OF THE INVENTION

Thus, based on the prior art instruments for biopsy sampling of tissue masses and the actual present state of this art, there exists a need for an instrument which can reliably obtain biopsy samples, which is simple in design, easy to use, and is cost effective.

Accordingly, I have invented an instrument for removing tissue samples of pre-determined size from a tissue mass where said instrument automatically penetrates, captures and allows the removal of said tissue sample for examination.

It is a principle object of this invention to provide an improved automated tissue sampling device with an improved needle set to effectively capture a core of tissue from the body.

It is yet another object of this invention to function in such a manner as to simplify the use of the invention in the biopsy procedure.

It is a further object of this invention to simplify the mechanical design of the invention by incorporating many of the functional parts and operational features into the disposable needle set to reduce the size, weight and complexity of the inventive handle mechanism.

It is a further object of this invention to provide a biopsy instrument which allows the placement of the detachable needle set into the body without the use of needle spacers and to allow the simple attachment of the needle set to the handle to perform the biopsy procedure.

It is another object of this invention to provide a biopsy instrument which allows the use of different needle sets that cycle at different distances and do not rely on the handle mechanism to set the distance the needle set travels.

It is a further object of this invention to provide a biopsy instrument which allows the actuation of the handle mechanism with a trigger that can be accessed from multiple and position thus allowing the physician free control of how the housing is held and not forcing the physician into only holding the device in certain ways.

In a further aspect of the invention, a system is enclosed which includes a needle set or needle cartridge and an extended use biopsy handle. As higher tolerance surfaces are located in a disposable cartridge, the handle can be simpler in design and more reliable, and the combination of a needle set or needle cartridge and handle can provide for a more reliable and repeatable biopsy procedure.

It is still a further object to provide a handle and needle set that automatically penetrates, captures, and allows the removal of a tissue sample without removing the needle set from the handle.

Accordingly, the present invention includes a needle set or needle cartridge having a first needle secured to a first hub and a second needle secured to a second hub. The first needle is positioned inside of the second needle, with the first needle and the second needle movable relative to each other. The first needle hub and the second needle hub are interlocking and the movement of the first needle relative to the second needle is restricted in a forward and a reversed direction by the hubs.

In another aspect of the invention, a biopsy handle includes a housing adapted for accepting a needle set or needle cartridge with the needle set or needle cartridge including a first needle and a second needle. The housing has a first driver which has a first cocked position and is adapted to drive the first needle. A second trigger is included which can hold the first driver in the first cocked position. The housing further has a second driver which has a second cocked position and which is adapted to drive the second needle. A second trigger is included which can hold the second driver in the second position. Releasing the first trigger causes the first driver to drive the first needle which causes the needle set or needle cartridge to release the second trigger in order to drive the second needle.

These and other objects of the invention will be apparent from the following descriptions, figures, and claims.

BRIEF DESCRIPTION OF THE FIGURES

The above noted advantages and other characteristic features of the present invention will be apparent from the accompanying drawings, and as pointed out in the following detailed description of the preferred embodiment of the invention in which references will be made to the accompanying drawings wherein like reference numerals designate corresponding parts and wherein;

FIGS. 1a1, 1a2, and 1a3 are top, side and front front elevation views of an embodiment of the biopsy handle instrument of this invention.

FIGS. 1b1, 1b2, and 1b3 are top, side, front, and elevation views of an embodiment of the needle set or needle cartridge of this invention. These figures depict the needle set in the locked position.

FIGS. 1c1, 1c2, and 1c3 are top views of the inventive needle set of FIG. 1b1 showing the sequence of actions that define the movement of the independent needle hubs as they function in the handle mechanism.

FIGS. 1d1, 1d2, and 1d3 are top, side and front elevation views of an embodiment of the biopsy handle instrument of this invention, similar to FIGS. 1a1, 1a2, and 1a3 with the lid that covers the handle mechanism removed.

FIGS. 1f1, 1f2, and 1f3 are top, side and front elevation views of the biopsy instrument of this invention with the lid that covers the mechanism removed. These figures depict the handle with the needle set in place.

FIG. 1h depicts yet another alternative embodiment of the needle set or needle cartridge with multiple handle engaging ports which are selectable in order to set different biopsy tissue collecting strokes of the needle set.

FIGS. 3a through 3e show a top view of an embodiment of the invention in different operational steps.

DETAILED DESCRIPTION OF THE PREFERRED EMBODIMENT

Figure 1E:
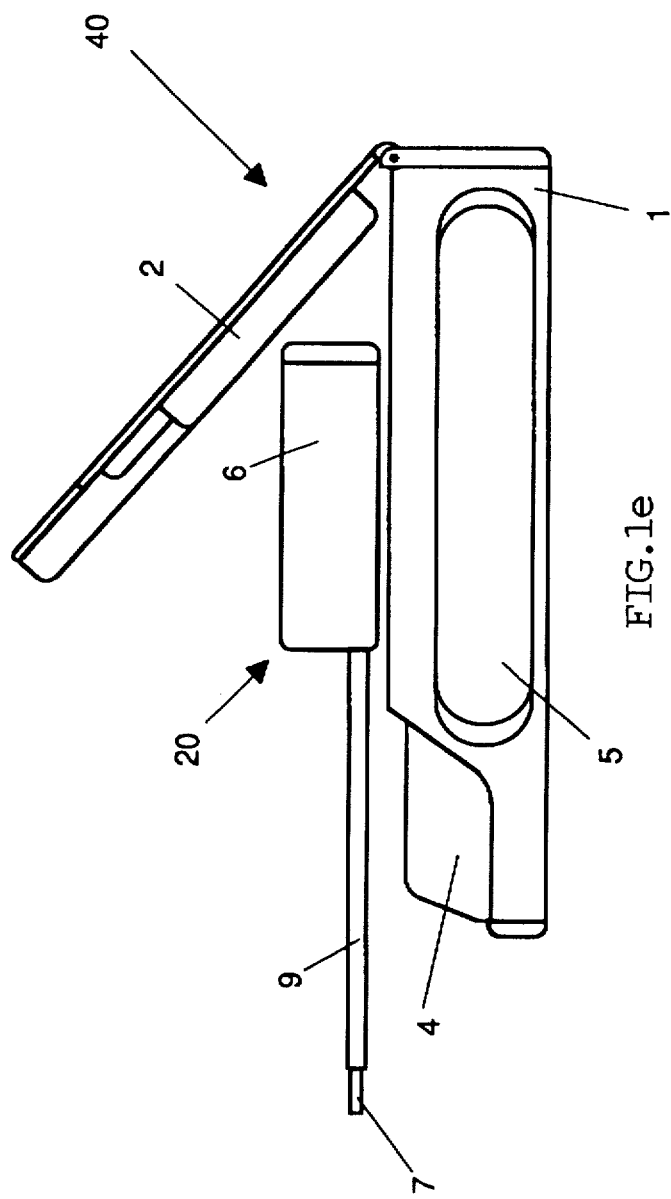
FIG. 1e is a side elevation view of the invention with the inventive needle set or needle cartridge positioned under the lid, ready to be placed down inside the handle mechanism of the invention.

For the purposes of promoting an understanding of the principles of the invention, reference will now be made to the embodiment illustrated in the drawings and specific language will be used to describe the same. It will nevertheless be understood that no limitation of the scope of the invention is thereby intended.

The instrument 40 (FIG. 3a) is of a spring powered, mechanical design. The needle set 20 (FIG. 1b1) is separate and disposable. The preferably disposable and preferably plastic hubs 6, 8, of the needle set 20 have been designed to operate as moving parts with the operational mechanism of the handle 1 (FIG. 1a1). By incorporating the functional aspects of the instrument 40 into the disposable needle set 20, the complexity of the handle mechanism has been reduced.

The hubs 6, 8 of the needle set or needle cartridge 20 act as the bearing surfaces of the moving parts within the handle, thus precluding the need of tight tolerance bearing, bushings or guide rods. The hubs 6, 8 act as the carriers for the needles 7, 9 in the handle. By making the disposable hubs function as part of the operational mechanism of the handle 1, the design is simplified by making the parts which experience high wear, disposable.

The needle set 20 is comprised of said interlocking hubs 6, 8. The interlocking hubs 6, 8 form a rectangular unit when the two needle hubs are locked together when tabs 30, 31 (FIG. 1c2), fit into slots such as slot 32 (FIG. 1b3), the hubs. The hubs 3, 8 are capable of moving axially in relation to each other to allow the sequencing of the individual needles 7, 9 in the handle 1.

Each hub 6, 8 contains a needle 7, 9. One hub 6 holds a stylet 7 that is a solid needle with a notch 12 ground in this distal end that is positioned coaxially inside the cannula 9. The 9 cannula is housed in the mating hub 8 which interlocks with the style hub 6. The cannula 9 is a hollow needle with a sharpened distal tip. The cannula 9 fits over the stylet 7 and when slid forward, towards the distal end of the stylet 7 during the biopsy procedure, cuts and captures the tissue inside the notched area 12 of the distal end of the stylet. Stylet hub 6 includes arms 6a and 6b extending therefrom. Cannula hub 8 includes arms 8a and 8b extending therefrom. Arm 6b is located between arms 8a and 8b while arm 8a is located between arms 6a and 6b. Stylet 7 is secured to arm 6b and is disposed inside cannula 9. Cannula is secured to arm 8a and projects through a port of arm 6a.

At the distal end of the stylet 7, a pointed tip facilitates the introduction of the needle set 20 into the tissue mass. The stylet 7 is positioned to protrude slightly beyond the end of the cannula 9 in the cocked position (FIG. 1c1). In the cocked position, the stylet 7 prevents tissue from entering the cannula 9 as the needle set 20 is introduced into the body.

The interlocking hubs 6, 8 of the needle set 20 form the above referenced rectangular block when the individual hubs 6, 8 are locked together. In this orientation, the needles 7, 9 are aligned axially to allow the manual placement of the needle set 20 in the body separate from the handle. This feature allows the needle set to be used in CAT scanning without the use of a separate "needle spacer" to orient the needles and hold them in the proper alignment for mounting into the handle 1.

In a preferred form, the inventive handle 1 includes a pair of cylindrical guide tubes 13, 14, each contains a spring backed drive block 15, 16 to which the needle set hubs 6, 8 are attached (FIG. 1d1).

The needle set hubs 6, 8 are attached to the drive blocks 15, 16 by placing them onto protruding pin 17, 18 in the drive block 15, 16 that are perpendicular to the axis of the guide tubes 13, 14. As is evident, there is a guide tube and drive block for each the stylet and cannula as these are actuated separately.

Each needle hub 6, 8 contains a channel 11a, 11b (FIG. 1b3) that is formed in the body of the hub and that runs parallel to the axis of the needles 7, 9. These channels accept the guide tubes 13, 14 of the handle 1. When the needle set 20 is sequenced in the handle 1, the needle hub channels 11a, 11b move axially along the guide tubes 13, 14 driven by the spring backed drive blocks 15, 16.

Figure 1G:
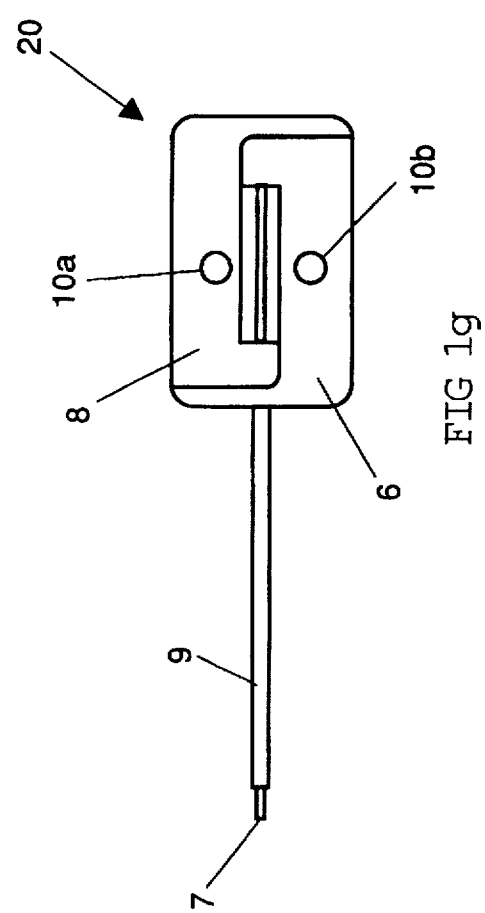
FIG. 1g depicts an alternative embodiment of the needle set or needle cartridge with the handle engaging ports repositioned in order to find a different stroke length for the needle set.
Figure 2A:
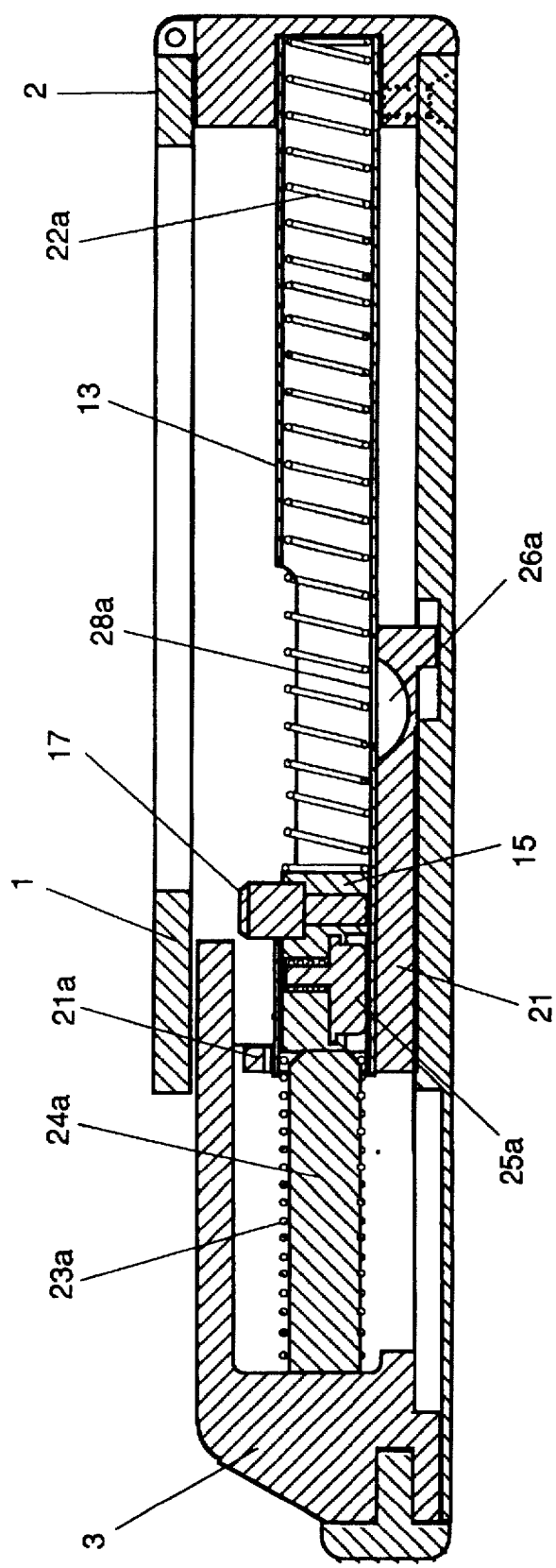
FIG. 2a is a cross-sectional view taken through line 2a–2a of FIG. 1f1 and shows the embodiment of the handle of the invention wherein a first driver for moving a first needle of the needle set is in an uncocked position.
Figure 2B:
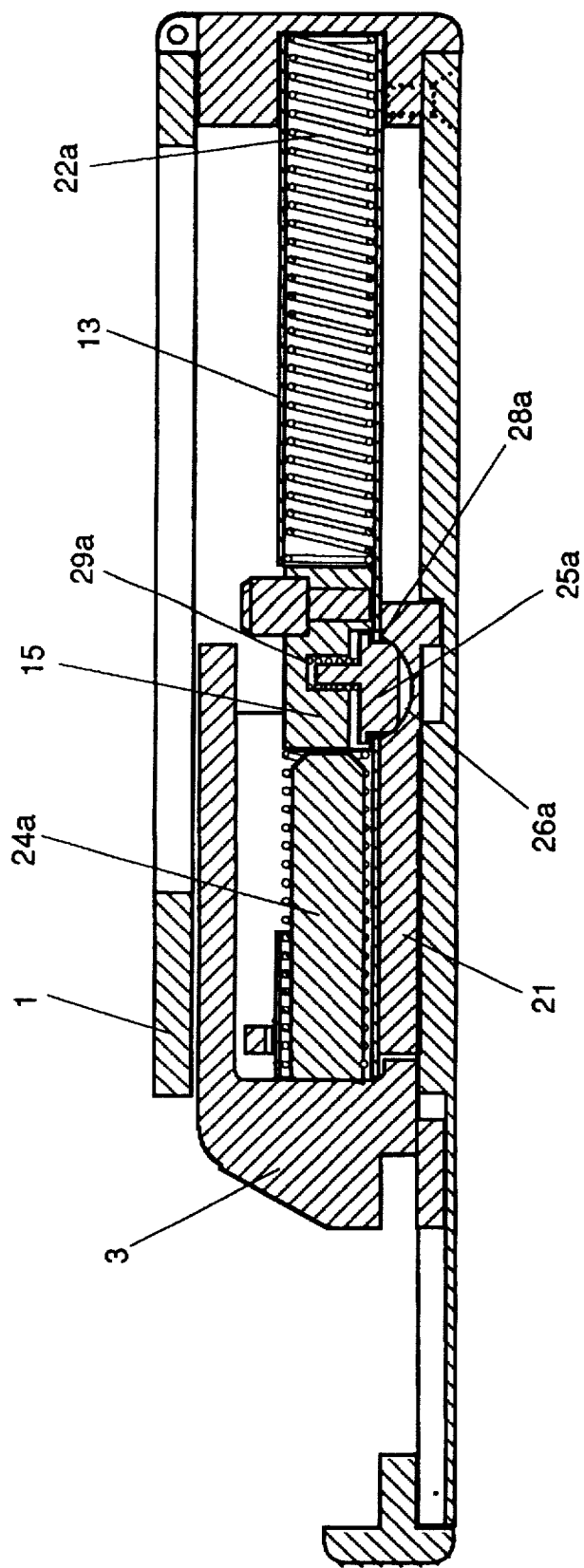
FIG. 2b shows a view similar to FIG. 2a but with the first driver in a cocked position.
Figure 2C:
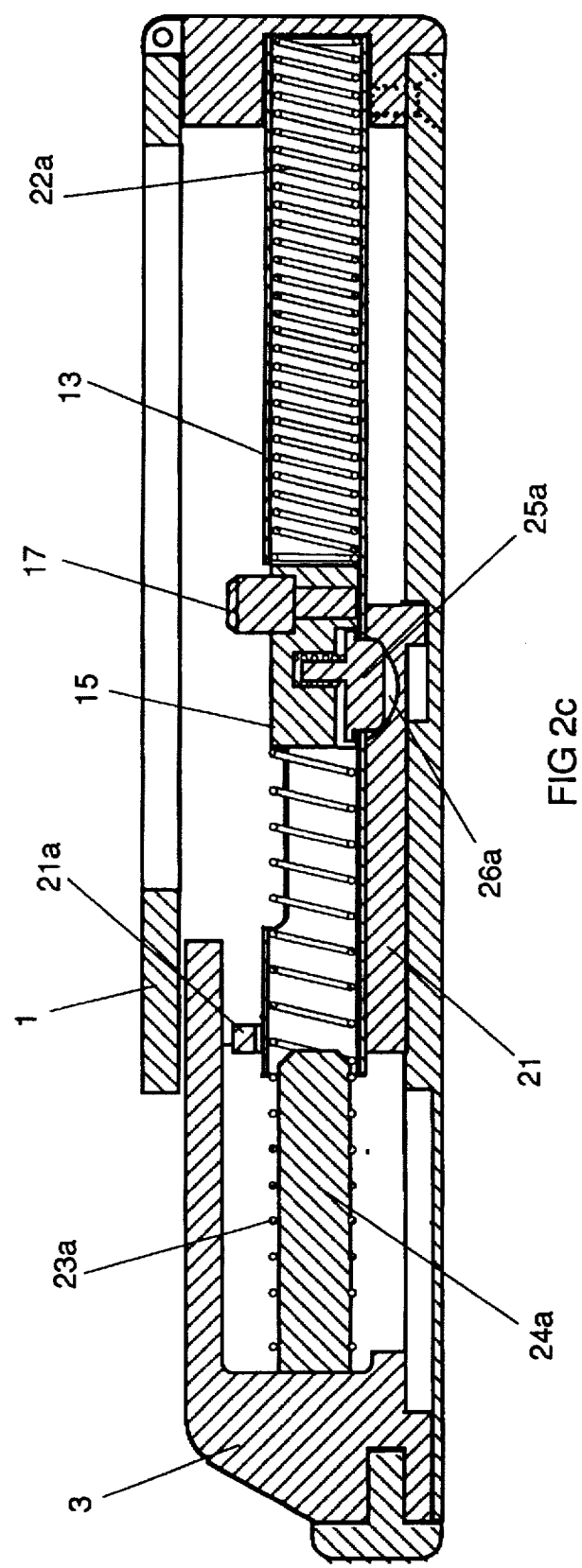
FIG. 2c is a view similar to FIG. 2b but with a thumb knob which was used to cock the mechanism return to its original position.
Figure 2D:
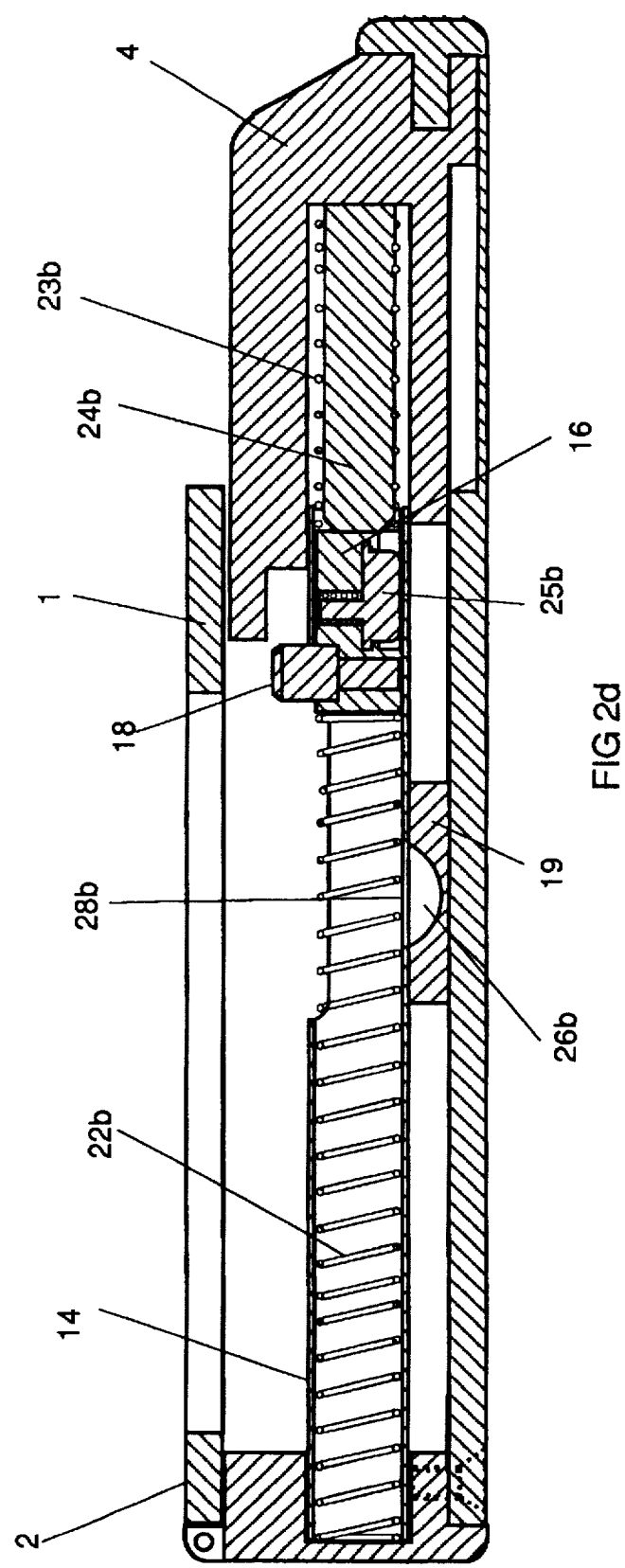
FIGS. 2d, 2e, and 2f taken through line 2f–2f of FIG. 1f1 and are similar to FIGS. 2a, 2b, and 2c, but show the movement of the second mechanism which drives the second needle of the needle set or needle cartridge.

The drive blocks 15, 16 are pushed backwards in the guide tube by means of thumb knobs 3, 4 (FIG. 1a1) that compress main springs 22a, 22b (FIGS. 2a, 2d). A locking mechanism 25a, 25b holds the drive blocks 15, 16 and main springs 22a, 22b in a spring compressed state. With both drive blocks 15, 16 pushed back into their locked state, the needle set hub 6, 8 can be positioned into the handle 1 in preparation for the sequencing of the needle set.

With the drive blocks 15, 16 locked in their spring compressed states (FIG. 3a) and the needle hub 6, 8 mounted onto the drive blocks 15, 16, the stylet 17 is positioned inside the cannula 9 and protrudes slightly out of the distal end of said cannula 9, thus preventing tissue from entering the cannula 9 during insertion into the body. Once the springs 22a, 22b are released, the individual drive block 15, 16 and needles 7, 9, are driven forward in a prescribed manner.

Each needle hub 6, 8 has a through hole 10a, 10b (FIG. 1b1) that accepts the protruding pin 17, 18 of the drive block 15, 16. Needle sets 20 can be provided with the location of these holes 10a, 10b, in a variety of distances from the distal end of the needle set (FIGS. 1b1, 1g, 1h). The position of the holes 10a, 10b and the distance from the distal end 10g of the needle set determines the distance the needle set will move forward in the body. This distance between the holes 10a, 10b in the hub 6, 8 and the distal end 10f of the needle hub determines the length of needle actuation, not the mechanism of the handle design. Thus, the position of the holes 10a, 10b in FIG. 1g ensure that the stroke of the stylet and cannula are shorter and thus the tissue sample collected is shorter. FIG. 1h has six holes (three hole sets) 10a, 10b, 10c, 10d, 10e, and 10f. Selection of any set of holes changes the stroke length of the needle set 20.

The handle contains two thumb knobs 3, 4 (FIG. 1b1). Each knob 3, 4 independently operates the drive block 15, 16 and main spring 22a, 22b of the stylet and cannula needle hubs 6, 8.

To use the invention in performing a biopsy procedure, the handle 1 must be prepared first. The thumb knob 3 for the cannula 9 is actuated first, placing the drive block 15 (for the cannula hub 8) in the locked position with the drive block 15 holding the main spring 22a in a compressed state. The thumb knob 4 of the stylet 7 is then actuated, placing the drive block 16 (for the stylet hole 6) in the locked position with the drive block 16 holding the main spring 22b in a compressed state. An internal spring 23a, 23b (FIGS. 2a, 2d) in each thumb knob 3, 4 returns it to a neutral state after the drive block 15, 16 has been pushed back into locked positions.

With both drive blocks 15, 16 in their locked positions and with their respective main springs 22a, 22b compressed, the locked needle set 20 can be positioned into the handle 1. To accomplish this, an outer lid 2 (FIG. 1e) that covers the moving parts of the handle 1 is raised and the locked needle hubs 6, 8 are positioned over the protruding pins 17, 18 of the drive blocks 15, 16. The needles 7, 9 fit down between the two thumb knobs 3, 4 and the lid 2 can then be closed.

The trigger 5 is moved and the first needle sequence is activated. The stylet 7 moves forward urged by the compressed spring 22b driving the drive block 16 forward. The protruding pin 18 from the drive block 16 which is located in the hole 10b of the stylet hub 6 moves the stylet hub 6 forward until it strikes the back of thumb knob 4, thus stopping its forward motion.

Prior to striking the back of the thumb knob 4, an arm 6a (FIG. 1b1) of the stylet hub 6 strikes an actuator bar 21a (FIG. 3b) of cannula trigger 21 (FIG. 2a) in the mechanism of the handle 1. The arm 6c of the stylet hub 6 moves the actuator bar 21a in the mechanism of the handle 1 forward, thus releasing the cannula drive block 15 from its locked position. When the actuator bar 21a is moved forward, the second needle sequence is activated. The cannula 3 moves forward urged by the compressed spring 22a, driving the drive block 15 forward. The protruding pin 17 from the drive block 15 which is located in the hole 10a of the cannula hub 8 moves the cannula hub 8 forward until it strikes the back stylet hub arm 6a which is against thumb knob 3, thus stopping its forward motion.

As the needles are released in sequence, the stylet 7 is pushed into tissue, the tissue is pierced and relaxes into the notched cut out.

When the cannula 9 is slid forward, the tissue in the notch of the stylet 7 is sliced off and retained in the notch 12 of the stylet 7.

Figure 3D:
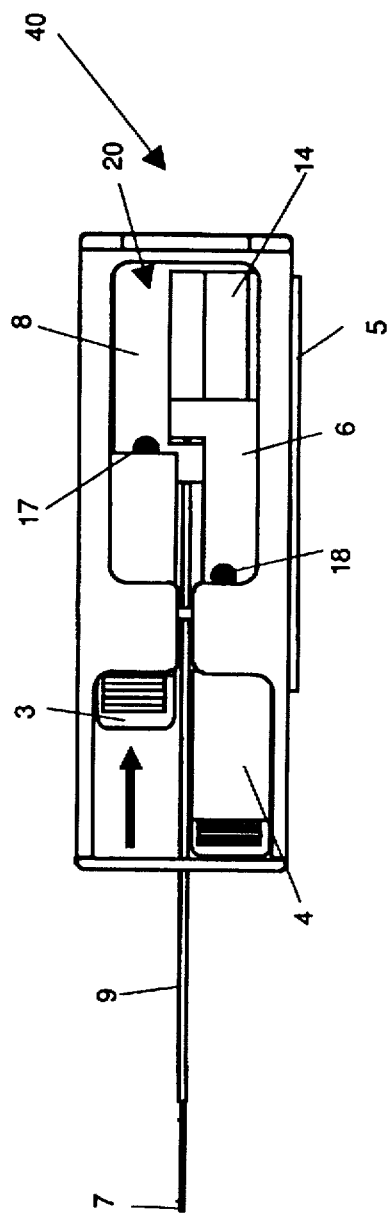
Figure 3E:
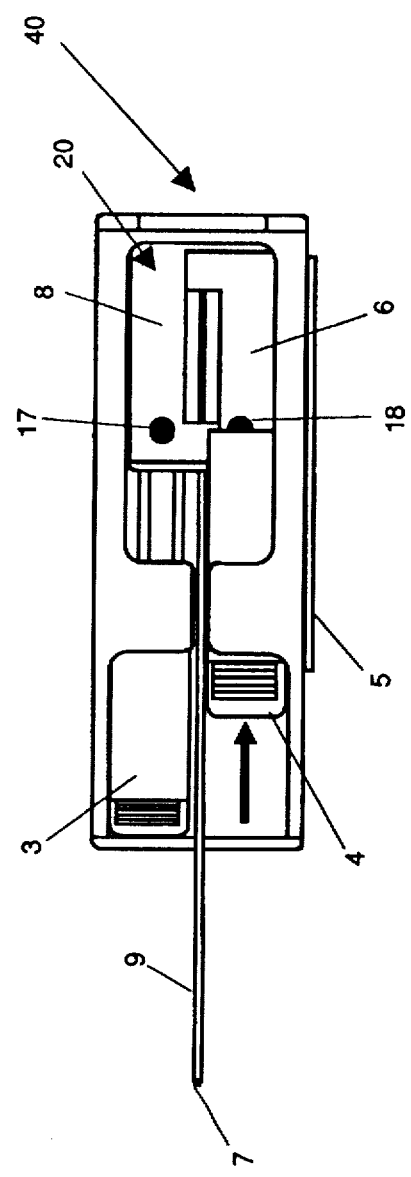

After withdrawal of the needle set 20 from the body, the cannula thumb knob 3 is activated and the drive block 15 and cannula 9 are retracted, the cannula 9 is moved backwards over the stylet 7, thus exposing the tissue core in the notched stylet 7 (FIG. 3d). This action allows the removal of the tissue core from the stylet 7 so it can be examined. Cocking the thumb knob 4 for the stylet 7 resets the instrument 40 for an additional biopsy attempt (FIG. 3e).

FIG. 1a1, 1a2, and 1a3 depict the major components of the inventive biopsy instrument 40. The main housing or handle 1 of the instrument has a cover lid 2 that shields the inner mechanism. The cannula and stylet thumb knobs 3, 4, respectively, are depicted. The trigger 5 (which is connected to stylet trigger extension 19), which when actuated by sliding it along the length of handle 1, begins the sequence of needle motions associated with the mechanism of the inventive device is also depicted.

FIGS. 1b1, 1b2, and 1b3 depict the inventive needle set 20. Item 6 is the stylet hub 6 and is attached to the stylet needle 7. The cannula hub 8 is attached to cannula needle 9. Each needle hub 6, 8 has a mounting hole 10a, 10b. Holes 10a, 10b are used to attach and drive the needles independently inside the handle 1 of the inventive biopsy device. The shape of the needle hubs 6, 8 create two parallel grooves 11a, 11b, that guide the motion of the needle hubs 6, 8 in the handle 1.

FIGS. 1c1, 1c2, and 1c3 depict the inventive needle set 20 showing the sequence of actions that define the movement of the independent needle hubs 6, 8 as they function. As the stylet needle hub 6 moves forward, the stylet needle 7 is moved forward in relation to the cannula needle 9. This forward motion of needle hub 6 and stylet 7 exposes the notched detail 12 as it protrudes past the end of cannula 9. The cannula hub 8 then moves forward urging the cannula needle forward coaxially over stylet 7, covering and capturing any tissue that lies in the notch 12, the needle 7.

FIGS. 1d1, 1d2, and 1d3 depict the handle 1 of the biopsy instrument of this invention, with the lid 2 that covers the mechanism removed. Inside housing 1 are two parallel tubes 13, 14. Inside tubes 13, 14 are two drive blocks 15, 16. Attached to these two drive blocks 15, 16 are two drive pins 17, 18. Pins 17, 18 are the devices that attach and drive the needle hubs 6, 8. Stylet trigger extension 19 is an extension of trigger 5. Trigger extension 19 is the device that releases block 16 from its spring compressing state, thus driving the first needle hub 6 forward. Cannula trigger 21 is activated by the stylet hub arms 6a, thus releasing the cannula hub 8 from the spring compressed position.

FIG. 1e, is a side view of the invention with the inventive needle set 20 positioned under the lid 2, ready to be placed down inside the handle 1 of the invention.

FIGS. 1f1, 1f2, and 1f3 depict the inventive needle set 20 positioned inside the handle 1 of the inventive biopsy device.

Considering drawings, FIGS. 2a, 2b and 2c, in detail, these drawings depict cross-section views of the embodiment of the handle 1 inventive biopsy instrument.

In FIG. 2a, a cross-section view of the inventive biopsy device is depicted cut on the axial centerline of the cannula drive tube 13. FIG. 2a shows the major components of the mechanism. The cannula thumb knob 3 contains a push rod 24a. Push rod 24a rests against the drive block 15 and is biased forward by the thumb knob return spring 23a. Inside the drive tube 13 are the drive block 15 and the main spring 22a. The drive block 15 contains the drive pin 17 and the catch block 25a. The catch block 25a is the device that holds the drive block 15 in position with the main spring 22a in compression. FIG. 2a also depicts the cannula trigger 21 and extension 21a which slides axially along the drive tube 13. A cutout 26a of the cannula trigger 21 is the actuating device for releasing the drive block 15 from its spring compressed position by releasing the catch block 25a from its locked position.

In FIG. 2b is a cross-section view of the inventive biopsy device handle 1 depicted cut on the axial centerline of the cannula drive tube 13. FIG. 2b shows the inventive biopsy device being in a cocked position. The cannula thumb knob 3 is depressed towards the distal end of the handle 1. The push rod 24a pushes the drive block 15 back, compressing the main spring 22a. As the cannula thumb knob 3 is depressed, it also moves the cannula trigger 21 back. As the drive block 15 moves backwards, it reaches a point where the catch block 25a is urged down into the drive tube slot 28a by the compressed catch spring 29a. When the catch block 25a is urged down through the drive tube slot 28a, the catch block 25a moves into the cutout 26a of the cannula trigger 21. The drive block 15 is held in place under the compression of the main spring 22a by the catch block 25a resting in the drive tube slot 28a.

In FIG. 2c, a cross-section view of the inventive biopsy device is depicted cut on the axial centerline of the cannula drive tube 13. FIG. 2c depicts the inventive biopsy device in the "ready to fire" position. The drive block 15 is locked in position by the catch block 25a, holding the main spring 22a in compression. The thumb knob return spring 22a has biased the cannula thumb knob 3 forward out of the way so that when the catch block 25a is released by the forward motion of the cannula trigger 21, the drive block 15 may move forward unimpeded.

In FIG. 2d, a cross-section view of the inventive biopsy device is depicted cut on the axial centerline of the stylet drive tube 14. FIG. 2d shows the major components of the mechanism. The stylet thumb knob 4 contains a push rod 24b. Push rod 24b rests against the drive block 16 and is biased forward by the thumb knot return spring 23b. Inside the drive tube 14 are the drive block 16 and the main spring 22b. The drive block 16 contains the drive pin 18 and the catch block 25b. The catch block 25b is the device that holds the drive block 16 in position with the main spring 22b in compression. FIG. 2d also depicts the stylet trigger extension 19 which slides axially below the drive tube 14. Cutout 26b of the stylet trigger extension 19 is the actuating device for releasing the drive block 16 from its spring compressed state by releasing the catch block 25b from its locked position.

Figure 2E:
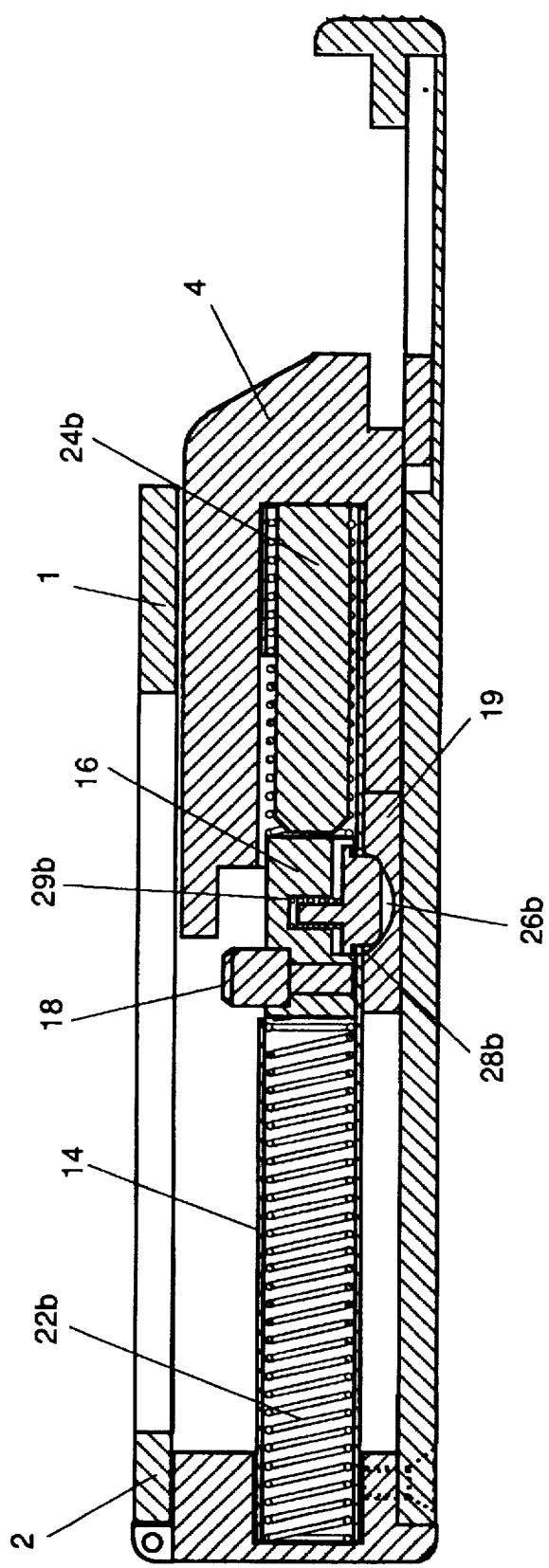

In FIG. 2e, a cross-section view of the inventive biopsy device is depicted cut on the axial centerline of the stylet drive tube 14. FIG. 2e shows the inventive biopsy device being cocked. The stylet thumb knob 4 is depressed towards the distal end of the handle 1. The push rod 24b pushes the drive block 16 back, compressing the main spring 22b. As the stylet thumb knob 4 is depressed, the drive block 16 moves backwards, and reaches a point where the catch block 25b is urged down into the drive tube slot 28b by the compressed catch spring 29b. When the catch block 25b is urged down through the drive tube slot 28b, the catch block 25b moves into the cutout 26b of the stylet trigger extension 19. The drive block 16 is held in place under the compression of the main spring 22b by the catch block 25b resting in the drive tube slot 28b.

Figure 2F:
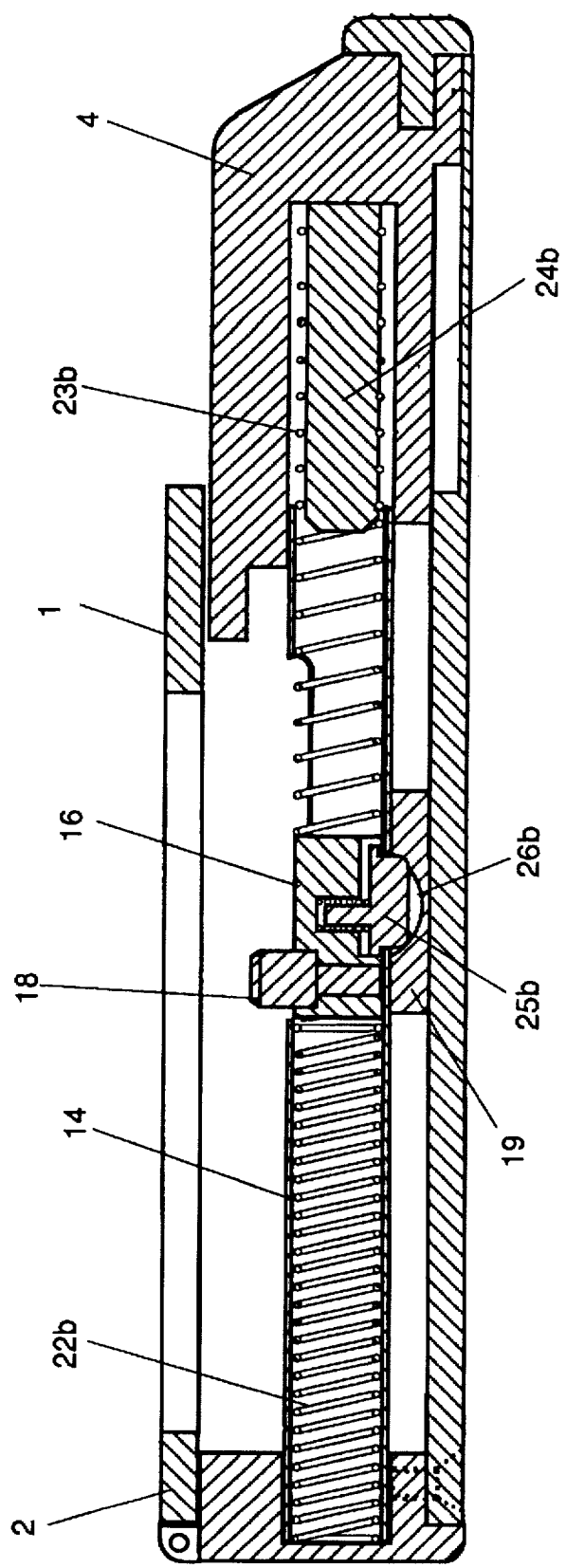

In FIG. 2f, a cross-section view of the inventive biopsy device is depicted cut on the axial centerline of the stylet drive tube 14. FIG. 2f depicts the inventive biopsy device in the "ready to fire" position. The drive block 16 is locked in position by the catch block 25b, holding the main spring 22b in compression. The thumb knob return spring 22b has biased the stylet thumb knob 4 forward out of the way so that when the catch block 25b is released by the forward motion of the stylet trigger 5 and the stylet trigger extension 19, the drive block 16 may move forward unimpeded.

FIG. 3a, is a top elevation view of the biopsy instrument 40 of this invention with the lid 2 that covers the mechanism removed. FIG. 3a depicts the device with needle set 20 in place. FIG. 3a depicts the handle 1 with the cannula needle hub 8 in the cocked position and the stylet needle hub 6 in the cocked position. FIG. 3a depicts that the forward motion of the trigger 5 releases the stylet hub 6 from its spring compressed position.

FIG. 3b, is a top elevation view of the biopsy instrument 40 of this invention with the lid 2 that covers the handle 1 removed. FIG. 3b depicts the handle 1 with the needle set 20 in place. FIG. 3b depicts the device with the cannula needle hub 8 in the cocked position and the stylet needle hub 6 moving forward. FIG. 3b depicts the forward motion of the stylet hub 6 striking the cannula trigger extension 21a, and pushing extension 21a forward, thus releasing the cannula hub 8 from the spring compressed position.

FIG. 3c is a top elevation view of the biopsy instrument 40 of this invention with the lid that covers the mechanism removed. FIG. 3c depicts the handle 1 with the needle set 20 in place. FIG. 3c depicts the handle 1 with the styles needle hub 6 in the fired position and the cannula needle hub 8 moving forward. FIG. 3c depicts that the forward motion of the cannula hub 8, stopped as it meets the stylet hub 6, thus finishing the cycle of needle actions.

In FIGS. 3d and 3e, the sequence of cocking the inventive mechanism is depicted. In FIG. 3d, the cannula thumb knob 3 is depressed towards the rear of the handle 1. This action pushes the cannula hub 8 back to its locked position. In FIG. 3e, the stylet thumb knob 4 is depressed towards the rear of the device. This action pushes the stylet hub 6 back to its locked position.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

INDUSTRIAL APPLICABILITY

Accordingly, the present invention provides for an inventive handle and needle set which simplifies the biopsy procedure and which is easy to use and make. The inventive needle set incorporates some of the operational features of the handle, thereby reducing or eliminating design needs and tolerances of the handle. The disposable needle set thus affords a simpler design for the handle, allowing the handle to be inexpensive to make and more compact.

Other features, aspects and objects of the invention can be obtained from a review of the figures and the claims.

It is to be understood that other embodiments of the invention can be developed and fall within the spirit and scope of the invention and claims.

I claim:

1. A needle system comprising:

a first needle secured to a first needle hub;

a second needle secured to a second needle hub;

said first needle positioned inside of said second needle with the first needle and the second needle movable relative to each other; and said first needle hub and said second needle hub interfere such that the movement of the first needle relative to the second needle is restricted in a forward and a reverse direction;

said first needle hub is C-shaped; and said second needle hub is C-shaped.

2. The system of claim 1 wherein:
said first needle is a solid stylet; and
said second needle is a hollow cannula.

3. The system of claim 1 wherein:
said first needle is a first hollow cannula; and
said second needle is a second hollow cannula.

4. The system of claim 1 wherein:
said first needle includes a groove adapted for collection a tissue sample; and
said second needle is a cannula which is adapted for severing the collected tissue sample so that the tissue sample can be removed from a biopsy site.

5. A needle system comprising:
a first needle secured to a first needle hub;
a second needle secured to a second needle hub;
said first needle positioned inside of said second needle with the first needle and the second needle movable relative to each other; and
said first needle hub and said second needle hub interfere such that the movement of the first needle relative to the second needle is restricted in a forward and a reverse direction;
said first needle hub has a first body with a first arm and a second arm extending from said first body;
said second needle has a second body with a third arm and a fourth arm extending from said second body; and
wherein said third arm is positioned between said first arm and second arm.

6. The system of claim 5 wherein:
said first needle is a stylet that is secured to said second arm and extends through the second needle which is a cannula; and
said second needle is secured to said third arm and extends through a port in said first arm.

7. The system of claim 5 wherein:
said second arm is position between said third arm and said fourth arm.

8. A needle system comprising:
a first needle secured to a first needle hub;
a second needle secured to a second needle hub;
said first needle positioned inside of said second needle with the first needle and the second needle movable relative to each other; and
said first needle hub and said second needle hub interfere such that the movement of the first needle relative to the second needle is restricted in a forward and a reverse direction;
at least one of said first and said second needle hubs has a tab which can interlock with at least one of the other of said first needle hub and said second needle hub.

9. A needle system comprising:
a first needle secured to a first needle hub;
a second needle secured to a second needle hub;
said first needle positioned inside of said second needle with the first needle and the second needle movable relative to each other; and
said first needle hub and said second needle hub interfere such that the movement of the first needle relative to the second needle is restricted in a forward and a reverse direction;
said first needle hub has a first body with a first handle engaging port positioned transverse to said first body; and
said second needle hub has a second body with a second handle engaging port positioned transverse to said second body.

10. The system of claim 9 including:
a first position wherein said first needle extends out from said second needle and a second position wherein said first needle is substantially withdrawn inside of said second needle; and
wherein said first handle engaging port is along side of said second handle engaging port with the system in the second position.

11. A needle system comprising:
a first needle secured to a first needle hub;
a second needle secured to a second needle hub;
said first needle positioned inside of said second needle with the first needle and the second needle movable relative to each other; and
said first needle hub and said second needle hub interfere such that the movement of the first needle relative to the second needle is restricted in a forward and a reverse direction;
said first needle hub has a first long arm and a second short arm;
said second needle hub has a third short arm and a fourth long arm; and
said third short arm is disposed between the first long arm and the second short arm and the second short arm is disposed between the third short arm and the fourth long arm.

12. The system of claim 11 wherein:
said system has a first position with the third short arm positioned against the first long arm and the second short arm positioned against the fourth long arm, and a second position with the second short arm against the third short arm; and
in the second position said first needle extends from said second needle.

13. A needle system comprising:
a first needle secured to a first needle hub;
a second needle secured to a second needle hub;
said first needle positioned inside of said second needle with the first needle and the second needle movable relative to each other; and
said first needle hub and said second needle hub interfere such that the movement of the first needle relative to the second needle is restricted in a forward and a reverse direction;
said first needle hub has a first elongated body;
said second needle hub has a second elongated body;
said first elongated body is substantially parallel to said second elongated body;
said first needle hub has a first groove which extends along said first elongated body;
said second needle hub has a second groove which extends along said second elongated body; and
said first groove is substantially parallel to said second groove.

14. The system of claim 13 wherein:
said first groove is adapted to engage a handle which can operate said system; and
said second groove is adapted to engage a handle which can operate said system.

15. A needle system comprising:

a first needle secured to a first needle hub;

a second needle secured to a second needle hub;

said first needle positioned inside of said second needle with the first needle and the second needle movable relative to each other; and said first needle hub and said second needle hub interfere such that the movement of the first needle relative to the second needle is restricted in a forward and a reverse direction;

said first needle hub has a first handle engaging port; and said second needle hub has a second handle engaging port.

16. A needle system comprising:

a first needle secured to a first needle hub;

a second needle secured to a second needle hub;

said first needle positioned inside of said second needle with the first needle and the second needle movable relative to each other; and said first needle hub and said second needle hub interfere such that the movement of the first needle relative to the second needle is restricted in a forward and a reverse direction;

said first needle hub has a first plurality of handle engaging ports; and said second needle hub has a second plurality of handle engaging ports.

17. A needle system comprising:

a first needle secured to a first needle hub;

a second needle secured to a second needle hub;

said first needle positioned inside of said second needle with the first needle and the second needle movable relative to each other; and said first needle hub and said second needle hub interfere such that the movement of the first needle relative to the second needle is restricted in a forward and a reverse direction;

the system including a first needle system and a second needle system;

each needle system including a first needle secured to a first needle hub and a second needle secured to a second needle hub;

each of said first needle hubs including a first handle engaging port and each of said second needle hubs including a second handle engaging port; and the first and second handle engaging ports of said first needle set are located in different locations on the first and second needle hubs of said first needle system than are the first and second handle engaging ports of said second needle set.

18. A needle system for collecting a tissue sample comprising:

a first needle secured to a first needle hub;

a second needle secured to a second needle hub;

said first needle positioned inside of said second needle with the first and second needles movable relative to each other;

said first needle hub having a first groove;

said second needle hub having a second groove, wherein said first groove and said second groove are parallel to said first and said second needles;

said first needle hub has a first handle engaging port which is skewed to said first and said second needles; and said second needle hub has a second handle engaging port which is skewed to said first and said second needles.

19. The system of claim 18 wherein:

said first and said second handle engaging ports are substantially perpendicular to said first and said second needles.

20. The system of claim 18 wherein:

said first and said second needles are located between said first handle engaging port and said second handle engaging port.

21. The system of claim 18 wherein:

said first needle hub is located along side of said second needle hub; and said first and said second needles are located for the most part between said first needle hub and said second needle.

22. The system of claim 18 wherein:

said first needle and said second needle are located between said first groove and said second groove.

23. A needle set comprising:

a first needle;

a first hub means for transporting said first needle;

a second needle;

a second hub means for transporting said second needle;

said first needle positioned inside of said second needle with the first hub means and said second hub means allowing the first needle and the second needle to move relative to each other;

said first hub means having first means for restricting the movement of the second hub means relative thereto; and said second hub means having second means for restricting the movement of the first hub means relative thereto.

24. A biopsy handle and biopsy needle set cartridge system comprising:

said biopsy needle set cartridge having:
   a. a first needle secured to a first needle hub;
   b. a second needle secured to a second needle hub;
   c. said first needle positioned inside of said second needle with the first and second needle movable relative to each other;
   d. said first needle hub having a first groove;

said second needle hub having a second groove, wherein said first groove and said second groove are parallel to said first and second needles;
   e. said first needle hub has a first biopsy handle engaging port which is skewed to said first and said second needles; and
   f. said second needle hub has a second biopsy handle engaging port which is skewed to said first and said second needles;

said biopsy handle having:
   g. a first needle drive mechanism with a first drive pin;
   h. a second needle drive mechanism with a second drive pin;
   i. said first needle drive mechanism being shaped in order to receive said first groove of said biopsy needle set cartridge thereover;
   j. said second needle drive mechanism being shaped in order to receive said second groove of said biopsy needle set cartridge thereover; and
   k. with said first drive pin being received in said first biopsy handle engaging port and said second drive pin being received in said second biopsy handle engaging port.

25. The system of claim 24 wherein:

said biopsy handle has a body with a front side; and said biopsy handle includes a port located substantially in the center of said front side, which port can receive said first and said second needles.

26. The system of claim 24 wherein:

said biopsy handle has a lateral side that is substantially parallel to said first needle and said second needle; and a trigger slidably mounted in said lateral side, said trigger slidable in order to actuate said needle set.

27. A biopsy handle comprising:

a first needle drive mechanism;

a second needle drive mechanism which is substantially parallel to said first needle drive mechanism;

said first needle drive mechanism is positioned along side of said second needle drive mechanism;

said first needle drive mechanism and said second needle drive mechanism each have a cocked position and a released position;

a first trigger mechanism;

a second trigger mechanism;

said first needle drive mechanism being held in said cocked position by said first trigger mechanism;

said second needle drive mechanism begin held in said cocked position by said second trigger mechanism;

said handle being adapted to receive a needle set;

said second trigger is adapted to be operated by said needle set in order to release said second needle drive mechanism from the cocked position after the first trigger releases said first needle drive mechanism from the cocked position;

a first drive pin extending from said first needle drive mechanism, which first drive pin is adapted for selectively positioning a first needle of a needle set; and a second drive pin extending from said second needle drive mechanism, which second drive pin is adapted for selectively positioning a second needle of a needle set.

28. A biopsy handle comprising:

a first needle drive mechanism;

a second needle drive mechanism which is substantially parallel to said first needle drive mechanism;

said first needle drive mechanism is positioned along side of said second needle drive mechanism;

said first needle drive mechanism and said second needle drive mechanism each have a cocked position and a released position;

a first trigger mechanism;

a second trigger mechanism;

said first needle drive mechanism being held in said cocked position by said first trigger mechanism;

said second needle drive mechanism begin held in said cocked position by said second said mechanism;

said handle being adapted to receive a needle set;

said second trigger is adapted to be operated by said needle set in order to release said second needle drive mechanism from the cocked position after the first trigger releases said first needle drive mechanism from the cocked position;

a first knob for urging said first needle drive mechanism to the cocked position; and a second knob for urging said second needle drive mechanism to the cocked position.

29. A biopsy handle comprising:

a housing adapted for accepting a needle set with a first needle and a second needle;

said housing having a first means adapted for driving the first needle of the needle set;

said housing having a second means adapted for driving the second needle of said needle set after said first means drives said first needle, which second means is adapted to be actuated by the needle set after the first means drives the first needle of the needle set; and a first drive pin extending from said first driving means, which first drives pin is adapted for selectively positioning a first needle of a needle set, and second drive pin extending from said second driving means, which second drive pin is adapted for selectively positioning a second needle of a needle set.

30. A biopsy handle comprising:

a housing adapted for accepting a needle set with a first needle and a second needle;

said housing having a first driver which has a first cocked position and which is adapted to drive the first needle;

a first trigger that can hold said first driver in the first cocked position;

said housing having a second driver which has a second cocked position and which is adapted to drive the second needle;

a second trigger that can hold the second driver in the second cocked position; and wherein releasing the first trigger causes the first driver to drive the first needle which causes the needle set to release the second trigger in order to drive the second needle;

said second trigger has a lever extending therefrom, which lever is adapted to be engaged by the needle set after the first driver drives the first needle in order to release said second trigger.

31. A biopsy handle comprising:

a housing adapted for accepting a needle set with a first needle and a second needle;

said housing having a first driver which has a first cocked position and which is adapted to drive the first needle;

a first trigger that can hold said first driver in the first cocked position;

said housing having a second driver which has a second cocked position and which is adapted to drive the second needle;

a second trigger that can hold the second driver in the second cocked position; and wherein releasing the first trigger causes the first driver to drive the first needle which causes the needle set to release the second trigger in order to drive the second needle;

said second driver is cylindrical in shape; and extending from said second trigger is a lever which wraps around the second driver and is accordingly adapted to be engaged by the needle set in order to release said second trigger.

* * * * *

UNITED STATES PATENT AND TRADEMARK OFFICE
CERTIFICATE OF CORRECTION

PATENT NO. : 5,752,923
DATED : May 19, 1998
INVENTOR(S) : Richard A. Terwilliger It is certified that error appears in the above-indentified patent and that said Letters Patent is hereby corrected as shown below:

Claim 27, line 28: After "mechanism" and before "held", delete "begin" and insert --being--

Claim 28, line 57: After "mechanism" and before "held" delete "begin" and insert --being--

UNITED STATES PATENT AND TRADEMARK OFFICE
CERTIFICATE OF CORRECTION

PATENT NO. : 5,752,923
DATED : May 19, 1998
INVENTOR(S) : Richard A. Terwilliger It is certified that error appears in the above-indentified patent and that said Letters Patent is hereby corrected as shown below:

Claim 28, line 58: After "second" and before "mechanism", delete "said" and insert --trigger--

Claim 29, line 15: After "first" and before "pin", delete "drives' and insert --drive--

Claim 4, line 9: After "collection" and before "a", insert --of--

Signed and Sealed this

Seventeenth Day of November, 1998

*Attest:*

BRUCE LEHMAN

*Attesting Officer*  *Commissioner of Patents and Trademarks*